United States Patent [19]

Bluestein et al.

[11] 4,116,993

[45] Sep. 26, 1978

[54] PROCESS FOR PRODUCING AROMATIC-CONTAINING SILICONE COMPOUNDS

[75] Inventors: Ben Alfred Bluestein, Schenectady; E. Robert Evans, Clifton Park, both of N.Y.

[73] Assignee: General Electric Company, Waterford, N.Y.

[21] Appl. No.: 812,954

[22] Filed: Jul. 5, 1977

[51] Int. Cl.$^2$ .......................... C07F 7/08; C07F 7/12; C07F 7/18
[52] U.S. Cl. ...................... 260/448.2 E; 260/448.8 R
[58] Field of Search ................. 260/448.2 E, 448.8 R

[56] References Cited

U.S. PATENT DOCUMENTS

| | | | |
|---|---|---|---|
| 3,053,872 | 9/1962 | Omietanski | 260/448.2 E |
| 3,202,634 | 8/1965 | Merker | 260/448.2 E X |

*Primary Examiner*—Paul F. Shaver
*Attorney, Agent, or Firm*—E. Philip Koltos; John L. Young; Frank L. Neuhauser

[57] ABSTRACT

An improved process for producing an aromatic containing silicon compound comprising reacting an aromatic organic compound of the formula $RX_a$ with a silicon compound of the formula $R_b'$ Si $Z_{4-b}$ in the presence of molar quantities of Mg and from 0.5 to up to 1 mole of a promoter which is preferably tetrahydrofuran per mole of the aromatic compound where R is preferably phenylene, X is chloro, a is 2, R' is preferably methyl, Z is alkoxy of 1 to 8 carbon atoms and b is equal to 2.

14 Claims, No Drawings

PROCESS FOR PRODUCING AROMATIC-CONTAINING SILICONE COMPOUNDS

BACKGROUND OF THE INVENTION

The present invention relates to an improved process for producing aromatic-containing silicon compounds and more particularly the present invention relates to producing alkoxy or chloro functional silphenylene compounds.

Grignard reagents are well known. Generally such reagents comprise a compound of the formula R″MgX where R″ is a hydrocarbon radical and X is chloro, iodo or bromo. As is well known in the presence of ether solvents such compounds will react with other halocarbon compounds to add a hydrocarbon group on to the R″ moiety. In a successful variation of such a reaction, there have been carried out reactions comprising reacting chlorobenzene in the presence of molar amounts of magnesium with chloro silanes to add on to the silane molecule the phenyl group of the chlorobenzene. Examples of such reactions are for instance those disclosed below:

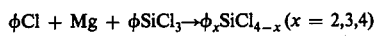  (a)

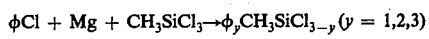  (b)

In the above reactions $\phi$ is phenyl. Although such reactions were attempted to a certain extent successfully in the past it was found that the yield were not as much as would be desired and usually require the presence of an ether solvent in copious amounts making such reactions hazardous, as well as expensive. Accordingly, it was highly desirable to be able to carry out the above reactions without the presence of a hazardous type of solvent and with as little an amount of solvent as possible so as to save in cost. Further, such reactions were particularly desirable to produce a silphenylene compound by reacting dichlorobenzene with a chloro silane so as to append silane groups to the divalent phenylene radical and produce a silphenylene compound. However, with the exception of the use of dibromobenzene as the reactant, it was found that such reactions would not result in a good yield of the desired silphenylene compound. It was found that when dichlorobenzene was utilized as the reactant that the second chlorine atom was not inclined to be substituted using the foregoing modified Grignard reactions.

Accordingly, various modified processes were utilized to prepare silphenylene compounds. Such modification of the Grignard reaction to produce silphenylene compounds is for instance to be found in Merker U.S. Pat. 3,202,634. As disclosed in Column 6 of the patent, the silphenylene compounds were obtained by the reaction of a dibromo or dichloro benzene with magnesium and a hydro silane to produce a hydrogenated silphenylene compound which in turn was converted to the silphenylene diol by reacting the silphenylene compound with a sodium hydroxide or potassium hydroxide in a mixture of alcohol and water. The resulting silphenylene diol could then be utilized as disclosed in Merker to produce block copolymers. However, in the initial reaction of producing the hydrogen containing silphenylene compound, the yields were not high and still necessitated the use of copious amounts of solvent; one specific such solvent being tetrahydrofuran. A more direct process in the production of silphenylene compounds is to be found in Omietanski U.S. Pat. No. 3,053,872. This patent discloses that in the production of silphenylene compounds of Formula 1 of the Patent $X_m'SiR_{4-m}^3$ could be reacted with dibromobenzene with molar amounts of magnesium so as to substitute the silane for the bromine atoms in the dibromobenzene. As defined in the Omietanski Patent $R^3$ stands for a monovalent hydrocarbon radical, while X' stands for halogen, alkoxy, phenoxy or an alkyl-substituted phenoxy radical and m is an integer having a value of from 1 to 3. Omietanski found that the modified Grignard reaction which is disclosed in the patent utilizing a dibromobenzene could be improved upon in that dichlorobenzene could be utilized as a reactant. Omietanski disclosed that such a process was possible over what had been done in the prior art in that a process where dichlorobenzene was reacted with molar amounts of magnesium and dimethyldichlorosilane to produce silphenylene compounds could be carried out by utilizing as a solvent copious amounts of tetrahydrofuran. Accordingly, Omietanski found that the desired chloro or alkoxy silphenylene compound could be obtained in good yields by the utilization of such a solvent. For instance in Example 2 Omietanski discloses the utilization of 500 milliliters of dry tetrahydrofuran per 147 grams of dichlorobenzene in his process. In Example 3 there is disclosed the use of 2000 milliliters of tetrahydrofuran and 441 grams of dichlorobenzene and in Example 5 the use of 750 milliliters of tetrahydrofuran and 147 grams of dichlorobenzene. Omietanski envisioned utilizing large amounts of tetrahydrofuran in his process to obtain the substitution of the chlorine groups in the para-dichlorobenzene in the modified Grignard reaction. While such was an innovation over the prior art, such a process has the disadvantage which includes also the process of the Merker Patent that tetrahydrofuran has to be utilized in copious amounts as a solvent. Note the discussion in Column 2 beginning with Line 17 of the Omietanski patent.

Accordingly, such use of copious amount of tetrahydrofuran has the disadvantage of increasing the cost of the process by utilizing as a solvent a material which is not one of the common solvents. Accordingly, it was highly desirable to find a process in which the silphenylene compounds could be obtained, without the use of a solvent or in the presence of as little amount of solvent as possible.

Accordingly, it was highly unexpected to find in view of Omietanski that the foregoing modified Grignard reaction could be carried out with promoter amounts of tetrahydrofuran, that is quantities of from 0.5 moles of tetrahydrofuran to up to 1 mole of tetrahydrofuran per mole of dichlorobenzene.

Accordingly, it is one object of the present invention to provide for an improved process for producing phenyl chlorosilanes utilizing a modified Grignard reaction with promoter amounts of tetrahydrofuran.

It is an additional object of the present invention to provide a process of producing silphenylene compounds utilizing promoter amounts of tetrahydrofuran.

It is a further object of the present invention to provide an improved process for producing phenyl chlorosilanes wihtout a solvent and in the presence of promoter amounts of tetrahydrofuran.

It is yet an additional object of the present invention to provide an improved process for producing silphenylene compounds by reacting a chlorosilane or an alkoxylated silane with dichlorobenzene in the absence of a solvent and in the presence of promoter amounts of tetrahydrofuran. These and other objects of the present invention are accomplished by means of the disclosure set forth hereinbelow.

SUMMARY OF THE INVENTION

In accordance with the above object there is provided by the present invention an improved process for producing an aromatic containing silicon compound comprising (a) reacting an aromatic organic compound of the formula $RX_a$ with a silicon compound of the formula $R_b'$ Si $Z_{4-b}$ in the presence of molar quantities of magnesium and in the range of from 0.5 to up to 1 mole of a promoter which is tetrahydrofuran per mole of the mono and dihalo aromatic compound and (b) distilling out the desired product where R is selected from the class consisting of monovalent and divalent mononuclear or binuclear aryl radicals, X is chlorine and $a$ is a whole number that varies from 1 to 4 and is preferably 2; R' in the foregoing formula being a radical selected from the class consisting of monovalent hydrocarbon radicals and is preferably methyl while Z is selected from the class consisting of halogen and hydrocarbonoxy radicals and is preferably an alkoxy radical of 1 to 8 carbon atoms while $b$ varies from 1 to 3 and is preferably 2.

While other catalytic promoters may be utilized to some extent such as diphenyl ether and para-dioxane, such catalytic promoters are in no sense equivalent to tetrahydrofuran. The other catalytic promoters such as diphenyl ether and para-dioxane while allowing the reaction to proceed result in small yields of the desired product. The foregoing reaction may be applied to any aromatic halogenated compound which is reacted with a silane. It is preferred to utilize the reaction in reacting a dichlorophenylene compound with a diorgano silane to produce the preferred silphenylene compounds of the instant case.

Tetrahydrofuran is the best promoter of the instant case and when it is utilized in the above process results in yields of as much as 50% or as much as 80% by weight of the desired silphenylene product with shorter reaction times at lower temperatures. With the tetrahydrofuran promoter of the instant case, which is utilized at a concentration of any where from at least 0.5 moles to up to 1 mole per mole of the paradichlorobenzene, the reaction is carried out at a general termperature range of anywhere from 100° to 200° C with a preferable temperature range being in the area of 100° to 160° C with the most preferable temperature range being 130° to 160° C at a period of time varying anywhere from 7 hours to 24 hours. As another aspect of the process disclosed above, the reaction can be initiated with advantage by utilizing as an initiator a crystal of an iodine compound or iodine itself. In an improvement of this procedure, the above reaction or process which starts with difficulty even with the addition of crystals of iodine or iodine compounds the reaction there may be initiated by taking anywhere from ¼ to ½ or more of the total reactants adding to such mixture from 0.1 to 1% by weight of total reactants of $Cu_2Cl_2$ as a reaction initiator heating the ingredients to a temperature of 100° C to 200° C to initiate the reaction and then after the reaction has been initiated and after a period of time varying from 1 to 3 hours adding to the mixture the rest of the ingredients. The use of cuprous chloride is preferred as a coupler initiator since in plant size quantities of reactants it functions more effectively as a coupler initiator in the instant process than crystals of iodine or iodine compound. It should also be noted from the above prior art, that the amount of magnesium that is utilized is equivalent to the molar amount of chlorine groups that are to be substituted in the dichlorobenzene or other aromatic reactant. Thus, if it is desired to produce a silphenylene compound, then the amount of magnesium that will be utilized in combination with dichlorobenzene is at least 2 moles of magnesium for the 2 moles of the chloro moieties in the benzene. Larger amounts of magnesium may be utilized, but serve only to preclude undesired coupling reactions.

DESCRIPTION OF THE PREFERRED EMBODIMENT

As indicated previously, the concept of the present invention can be applied to more general reactions than the preparation of silphenylene compounds. For instance it can be applied to the reactions mentioned previously which are as follows:

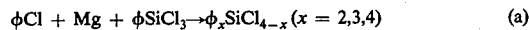  (a)

  (b)

In the above formulas $\phi$ is phenyl.

In the above reaction, it is preferred that there be utilized at least one mole of magnesium per mole of chlorine to be substituted and the promoter amounts of tetrahydrofuran. The promoter amounts of tetrahydrofuran is to be understood to be anywhere from 0.5 moles to up to 1 moles but not exceeding 1 mole per mole of the chlorobenzene or the aromatic chloride reactant. If less than 0.5 moles of tetrahydrofuran are utilized, then the reaction will not proceed to completion and if more than 1 mole of tetrahydrofuran is utilized in the above reactions then additional amounts of tetrahydrofuran does not improve the reaction while at the same time the excess amount may act to reduce the amount of yield of the desired product.

More generally, in concept of the instant process there is involved the reaction of an aromatic organic compound of the formula $RX_a$ with a silicon compound of the formula, $R_b'$ Si $Z_{4-b}$ as stated previously.

Generally, in the above formula R is selected from the class consisting of monovalent and divalent mononuclear and binuclear aryl radicals. Examples of such radicals being phenyl and naphthyl, methylpehnyl, ethylphenyl, etc. where $a$ varies anywhere from 1 to 4 and is preferably 2. In the second formula R' is preferably selected from the class consisting of monovalent hydrocarbon radicals and halogenated monovalent hydrocarbon radicals such as alkyl radicals of 1 to 8 carbon atoms, methyl, ethyl, propyl; cycloalkyl radicals such as cyclohexyl, cycloheptyl, etc.; mononuclear aryl radicals such as phenyl, methylphenyl, ethylphenyl, etc.; alkenyl radicals such as vinyl, allyl, etc. and halogenated alkyl radicals such as 3,3,3-trifluoropropyl, etc. Most preferably R' is selected from alkyl radicals of 1 to 8 carbon atoms and most preferably methyl or ethyl. Z in the above formulas can be selected from halogen and hydrocarbonoxy radicals; examples of halogen radicals being bromo, chloro with chloro being the most preferred. With respect to the hydrocarbonoxy substituent groups for Z examples of such radicals are alkoxy radicals of 1 to 8 carbon atoms, phenoxy radicals including methylphenoxy, ethylphenoxy, etc. and other hydrocarbonoxy radicals. Most preferably the Z radical is selected from chloro or alkoxy radicals of 1 to 8 carbon atoms such as methoxy, ethoxy, propoxy, etc. In the preparation of the most preferred silphenylene compounds, it is preferred that Z be an alkoxy radical of 1 to 8 carbon atoms. In the foregoing formula b may vary anywhere from 0 to 3 and is most preferably 2, such that there are two Z radicals and two R' radicals in the silane of the foregoing formula.

Most preferably in the process of the instant case R is a phenylene radical and X is a chloro radical with $a$ equal to 2 such that you have a para-dichlorobenzene compound. Such an aromatic organic compound, that is para-dichlorobenzene may be reacted and is preferably reacted in the production of silphenylene compositions with compounds in which R' is an alkyl radical of 1 to 8 carbon atoms and most preferably methyl and Z is an alkoxy radical of 1 to 8 carbon atoms with b being equal to 2. It should be understood that even though the comments below will be discussed with reference to the reaction of dichlorobenzene that such comments will apply to the other more general reactants discussed previously.

Accordingly, the dichlorobenzene will be reacted with molar amounts of the silane compound. If it is desired to substitute one silicon group for each chloro group in the para-dichlorobenzene then there is preferably utilized at least 2 moles of the silane reactant per mole of para-dichlorobenzene. If less than 2 moles of the silane compound is utilized per mole of the dichlorobenzene then the substitution of both chlorine atoms in the dichlorobenzene will be incomplete as can well be understood. In addition per mole of the chlorine to be substituted in the aromatic organic compound, there must be at least 1 mole of magnesium otherwise the preferred Grignard reagent will be obtained in less than the optimum amounts and the reaction will not be able to proceed to completion.

Accordingly, in the case of the preparation of silphenylene compounds there will be present at least 2 moles of the silane compound per mole of para-dichlorobenzene and there will be present at least 2 moles of magnesium per mole of the para-dichlorobenzene. It should be noted that the silphenylene intermediates that are obtained by the process of the instant case have a special utility in being utilized as intermediates to produce silphenylene block copolymers as disclosed in the foregoing Merker U.S. Pat. No. 3,202,634. The other more general phenyl silane products of the instant case have uses as intermediates in producing phenyl containing polymers that may be utilized to produce heat vulcanizable silicone rubber compositions or room temperature silicone rubber compositions.

Accordingly, with the foregoing amount of reactants that are necessary in the process of the instant case, there must be utilized anywhere from 0.5 to up to 1 mole of a promoter which is tetrahydrofuran. From the use of this promoter there is obtained a maximum yield of the desired silphenylene product even with amounts of tetrahydrofuran as small as 0.5 moles per mole of the para-dichlorobenzene. Accordingly there may be utilized anywhere from 0.5 moles tetrahydrofuran to up to 1 mole of the tetrahydrofuran per mole of the aromatic organic compound or more specifically para-dichlorobenzene. If less than 0.5 moles is used then the reaction will not reach completion if more than 1 mole of tetrahydrofuran is utilized, it does not serve a useful purpose and indeed may decrease the yields. More preferably there is utilized amounts of tetrahydrofuran at a concentration of 0.6 to 0.9 moles per mole of the para-dichlorobenzene. After the tetrahydrofuran has been added to the ingredients and the ingredients thoroughly mixed then to initiate the process, it is necessary to elevate the temperature of the ingredients to a range of anywhere from 100° to 200° C for a period of time varying anywhere from 7 to 24 hours. At that temperature the reaction will proceed to obtain the desired reaction product.

It should be noted that in the above reaction only tetrahydrofuran has been found to give the excellent results with a maximum yield in the promoter concentrations as was discussed before. Other types of promoters may produce some product but the yield is low, as well as requiring excessive reaction time. Generally, as has been pointed out above in the process of the instant case a reaction time of anywhere from 7 to 24 hours is adequate. A shorter reaction time may be utilized, but generally the reaction has not reached completion at that point. Further, reaction periods of more than 24 hours do not increase the yield of the desired product. It should be noted, of course, that if a reaction temperature of less than 100° C is used then the reaction may take a very long period of time. Preferably the temperature is maintained within the above range for a period of anywhere from 7 to 15 hours to obtain the desired product in the maximum yield. With the preferred quantities of reactants with the preferred conditions there results yields of anywhere from 50 to as high as 80% or more of the desired silphenylene product. It is preferred that the reaction temperature be varied anywhere in the area of 100° to 160° C and more preferably at a temperature of anywhere from 130° to 160° C. It has been found that the above are the best reaction temperatures for the preparation of silphenylene compounds from para-dichlorobenzene and usually result in the maximum yield of product at reaction times of anywhere from 7 to 15 hours as stated previously. It should be noted and as stated previously that with tetrahydrofuran the yield of the desired silphenylene product that is obtained from para-dichlorobenzene is at least 50% and generally may vary anywhere from 60 to 80% or higher depending upon the use of optimum reaction conditions. It should be noted that the reaction can be carried out at the atmospheric pressure or it can be carried out at super atmospheric pressure with a minor difference in results. In the process of the instant case, it is generally desired to mix the magnesium with the aromatic organic compound and the tetrahydrofuran or the para-dichlorobenzene first, and then to add the silane of the above formulas at the appropriate concentration. However, the order of mixing the ingredients is not important. The silane should also be thoroughly mixed with the magnesium and the aromatic organic compound. The reaction is then heated above 100° C in a closed vessel and the reaction is allowed to proceed to obtain the desired yield of the product. It has been found that this reaction has some difficulty in being initiated even at the elevated temperatures of above 100° or 130° C. Accordingly, it is common to insert into the reaction mixture prior to raising the temperature or during the heating of the reactants some crystals of a common reaction initiator. Such reaction initiator for the process of the instant case can comprise of a few crystals of iodine or a iodine compound such as methyl iodide. It should be noted that it is preferred that there be agitation of the raction mixture constantly during the reaction period so as to minimize the reaction time and maximize the yield.

Although such agitation is not strictly necessary for the process of the instant case to proceed; nevertheless, if it is omitted the reaction period is unnecessarily prolonged and as high a yield is not obtained. It has also been found that with respect to the reaction initiation that the utilization of crystals of iodine and iodide compounds performs satisfactorily when large scaled batches are reacted, however, the yield is not as high as could be desirable.

Accordingly, it is highly desirable in order to carry out the foregoing process to find a reaction coupler which also serves to mollify the exothermicity and increase product yield. Accordingly, one method that has been developed in the instant case is to utilize as a reaction coupler of anywhere from 0.1 to 1% by weight of the total reactants of cuprous chloride. Although, lower amounts of cuprous chloride may be utilized the yield is not as high as would be desired. Although larger amounts of cuprous chloride may be utilized as a coupler such larger amounts do not serve a useful purpose and may contaminate the reactants. In one method of utilizing such a reaction coupler, the cuprous chloride may simply be added to reactants after they have all been mixed and then with agitation increase the temperature in the ranges indicated previously. A more preferred method which seems to initiate the reaction at a faster rate when it is carried out in plant-size quantities is to add the foregoing amount of cuprous chloride to anywhere from ¼ to ½ or more of the ingredients in the reaction vessel and to heat this mixture to the reaction temperature with agitation. After the reaction has initiated, then over a period of time of 1 to 4 hours there is continually added the rest of the portion of the ingredients to the reaction vessel to allow the reaction to proceed to completion. Accordingly, it is highly desirable with this improvement in increasing the yield of the process of the instant case to add the amounts of cuprous chloride as mentioned previously to anywhere from ¼ up to ½ of the total mixed ingredients, allow this portion to heat up as a result of the exothermic reaction and during a period of time of 1 to 3 hours or as long as 5 hours continuously add the rest of the portion of the ingredients slowly with the necessary heating and agitation to allow the reaction to proceed to completion. It has been found that by utilizing such a coupler procedure that the reaction period is substantially minimized and the highest yield of the desired product is obtained. It should be noted that the cuprous chloride can be added to the ingredients in the vessel in any order after the adding of the crystals of iodine or iodine compound to the reaction mixture. After the reaction has reached completion, then the desired silphenylene compound or other silyl aromatic compound may be separated out from the mixture by well known distillation procedures, with the residue being discarded or reprocessed. There can be obtained when the para-dichlorobenzene reactant is utilized a silphenylene intermediate product having the formula,

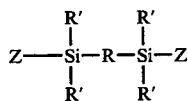

where R, R' and Z are as previously defined. It should be understood that to obtain the maximum yield of the desired silphenylene compound or as maximum a yield as possible in the shortest period of time than the preferred conditions and reactants be utilized as discussed above. Further, without the use of the reaction initiator and specifically the cuprous chloride, the yield will be somewhat low unless a prolonged period of time is utilized for a reaction period. Such prolonged periods of time are undesirable since they make an uneconomic use of plant facilities. It should also be noted that once the reaction is initiated that the reaction which is exothermic will continue for a period of time varying anywhere from 1 to 4 hours in most cases without external heating in the temperature range of 100° to 200° C. After this period of time there would be required that the reaction mixture be heated, to maintain the reaction ingredients at the desired temperature level of 100° to 200° C and more preferably in the range of 100° to 160° C. In any case by utilizing the proper quantities of the ingredients specified above with the utilization of the levels of tetrahydrofuran discussed previously, there is obtained in the shortest period of time, the highest yield of silphenylene compound. It should be noted that while excess amounts of magnesium may be utilized in the instant process, such serves no useful purpose either in increasing the yield of the desired product or in increasing the speed of the reaction discussed previously, however, the excess magnesium does include the above ring coupling reaction which will lower product yield. In the same vein, if there is utilized excess amounts of the silane reactant no advantage is obtained thereby. In fact the use of excess amounts of magnesium and of the silane reactant only increase the expense of the process. However, there must be utilized the necessary concentration of the silane compound and of the magnesium to obtain the desired substitution in the para-dichlorobenzene or other aromatic silicon compound in accordance with the disclosure above.

Thus, in the case of para-dichlorobenzene to produce silphenylene compounds there must be utilized at least 2 moles of magnesium and at least 2 moles of the silane reactant to obtain the desired silphenylene product in high yields. It should be noted that it is not known why tetrahydrofuran acts as a promoter in the instant modified Grignard reaction. It was discovered by Omietanski that tetrahydrofuran could be utilized as a solvent and because of its solvent capabilities resulted in a modified Grignard reaction in which the chlorine groups in the para-dichlorobenzene could be substituted by silyl moities. Although Omietanski does not state so, it appears by his disclosure that by the use of the term solvent he meant that by the use of excess amounts of tetrahydrofuran which acted as a super solvent there was obtained intimate contact between the magnesium, the chlorine groups in the p-dichlorobenzene and the silane reactant. It has now been found through the instant invention that in fact tetrahydrofuran does not function as a solvent in the modified Grignard reaction of the present case. It has been the discovery of the instant case, that tetrahydrofuran acts as a promoter to the magnesium and not as a solvent to permit contact between the ingredients. Accordingly, it is postulated that tetrahydrofuran in the process of the instant case enhances the activity of the magnesium and enhances the activity of any magnesium reagent that is formed such that the chlorine groups on the p-dichlorobenzene are easily substituted by silyl moities in the silane reactant.

Accordingly, but for this enhancement of the activity of the magnesium, it should be noted that tetrahydrofuran is not needed as a solvent, and performs its functions in the small quantities recited in the instant specification. It should be noted that the above is a theory that is set forth in the basis of the work that will be set forth in the following examples. The examples below are given for the purpose of illustrating the conception and reduction to practice of the instant invention. They are not given for any purpose or setting the limits or defining the scope of the instant invention.

EXAMPLE I

In the data given in this Example ml. stands for milliliter g stands for grams and m stands for mole. Accordingly, into a 500 ml flask equipped with a stirrer, condenser, thermometer, nitrogen inlet, there was placed was a cut below 135° C at 3 mm Hg, 28 g, a cut at 140°–142° C at 3 mm vacuum, 71 g; a cut at 140°–150° C, 3 mm of vacuum, 3 g; and a residue of 12 g. The 140°–142° cut under Vapor Chromatography scan indicated that it was the desired dipropoxytetramethyl-disilylphenylene compound or p-bis-(propoxydimethyl-silyl) benzene, which represents a 76% yield of product. In the experiments set forth in Table I below, the results of additional experiments which were run under conditions similar to that recited above, are set forth. In Table I Me stands for methyl; Et stands for ethyl; Pr stands for propyl; φ stands for phenyl; g stands for gram; m stands for mole; THF stands for tetrahydrofuran and VPC stands for Vapor Phase Chromatography.

TABLE I

| Expt. No. | Reactants | Catalyst-Promoter | Reaction Conditions | Results |
|---|---|---|---|---|
| | Summary of Experiments Relating to Disilphenylene Syntheses | | | |
| 1 | $Me_2Si(OPr)_2$, 17.6 g (0.1m)<br>p-$ClC_6H_4Cl$, 5.8 g (0.04m)<br>Mg, 2.0 g (0.08m) | Crystal $I_2$<br>$(Me_2NCH_2)_2$, 1.6 cc.<br>$O_2O$, 20 cc | Relfux 168–192°/15 hr | Much $(PrOSiMe_2)_2C_6H_4$<br>some $ClC_6H_4SiMe_2OPr$<br>(VPC) |
| 2 | $Me_2Si(OEt)_2$, 29.6 g (0.2m)<br>p-$ClC_6H_4Cl$, 7.3 g (0.05m)<br>Mg, 2.5 g (0.1m) | Crystal $I_2$<br>$O_2O$,25 cc. | Reflux 134°/9 hr. | No reaction |
| 3 | $Me_2Si(OPr)_2$, 35.2 g (0.2m)<br>p-$ClC_6H_4Cl$, 7.3 g (0.05m) | Crystal $I_2$<br>$(Me_2NCH_2)_2$, 0.75 g | Reflux 155/6 hr. | No reaction |
| | Mg, 2.5 g (0.1m) | ten $O_2O$, 20 cc. | Reflux 168–180°/8 hr. | Much $(PrOSiMe_2)_2C_6H_4$<br>(VPC) No change<br>after 12 Hr. more<br>reflux. |
| 4 | $Me_2Si(OPr)_2$ 300 g (1.7m) | Crystal $I_2$ | Reflux to 192°/31 hr. | Distill 140-2° (3mm)<br>68 g. |
| | p-$ClC_6H_4Cl$, 73 g (0.5m)<br>Mg 44 g. (1.8m) | $(Me_2NCH_2)_2$, 8 cc<br>$O_2O$, 200 cc. | | (44% yield of (PrOSi<br>$Me_2)_2C_6H_4$ |
| 5 | $Me_2Si(OPr)_2$ 26.4 g (0.15m)<br>p-$ClC_6H_4Cl$, 7.3 g (0.05m) | Crystal $I_2$<br>THF, 1 cc. | Reflux 150–6°/13 hr. | Some $ClC_6H_4SiMe_2OPr$<br>(VPC) |
| | Mg, 4.8 g (0.2m) | then add THF | Reflux 125°/4 hr. | Much $(PrOSiMe_2)_2C_6H_4$<br>(VPC) |
| 6 | $Me_2Si(OPr)_2$, 27 g, (0.15m)<br>p-$ClC_6H_4Cl$, 7.3 g (0.05m)<br>Mg, 4.8 g (0.2m) | Crystal $I_2$<br>THF, 3.6 g<br>(0.05m) | Reflux 123—6/2 hr. | Much $8PrOSiMe_2)_2C_6H_4$<br>(VPC)<br>No change after 10 hr.<br>more reflux |
| 7 | $Me_2Si(OPr)_2$, 132 g (0.75m)<br>p-$ClC_6H_4Cl$, 44 g (0.3m)<br>Mg, 18 g, (0.75m) | Crystal $I_2$<br>THF, 21.6 g (0.3m) | Reflux 120–144°/13 hr. | Distill 71 g at 140-2°<br>(3 mm.)<br>$C_6H_4$ |
| 8 | $Me_2Si(OEt)_2$, 111 g (0.75m)<br>P-$ClC_6H_4Cl$, 44 g (0.3m)<br>Mg, 18 g (0.75m) | Crystal $I_2$<br>THF, 22 g (0.2m) | Reflux to 125°/11 hr.<br>with approx. 20% Cl | Mostly $(EtOSiMe_2)_2C_6H_4$<br><br>$C_6H_4SiMe_2OET$ (VPC) |
| 9 | $Me_2Si(OEt)_2$, 111 g (0.75m)<br>p-$ClC_6H_4Cl$, 44 g (0.3m)<br>Mg, 18 g (0.75m) | Crystal $I_2$<br>THF, 43 g (0.6m) | Reflux to 106°/12 hr. | Distill 42 g<br>$(EtOSiMe_2)_2C_6H_4$<br>at 104–129°0 (3 mm.)<br>(50% yield) |
| 10 | $Me_2Si(OPr)_2$, 194 g (1.1m)<br>p-$ClC_6H_4Cl$, 73 g (0.5m)<br>Mg, 26 g (1.1m) | Crystal $I_2$<br>THF, 36 g (0.5m) | Reflux 94–117°/7 hr. | Distill 87 g at<br>141° (3mm.)<br>(56% yield) |
| 11 | $Me_2Si(OEt)_2$, 148 g (1m.)<br>p-$ClC_6H_4Cl$, 44 g (0.3m)<br>Mg, 18 g (0.75m) | Crystal $I_2$<br>THF, 57 g (0.8m) | Reflux to 127°/26 hr. | Distill 47 g at 81 –<br>121° (1-2 mm.)<br>(56% yield) |
| 12 | $Me_2Si(OEt)_2$, 148 g (1m)<br>p-$ClC_6H_4Cl$, 44 g (0.3m)<br>Mg, 18 g (0.75m) | Crystal $I_2$<br>THF, 86 g (1.2m) | Reflux 106–121°/27 hr. | Much $(EtOSiMe_2)_2C_6H_4$<br>(VPC)<br>no residual $C_6H_4Cl_2$ |
| 13 | φCl, 22 g (0.2m)<br>$MeSi(OEt)_3$, 18 g (0.1m)<br>Mg 4.9 g (0.2m) | Crystal $I_2$<br>THF, 7.2 g (0.1m) | 95–116°/20 hr. | Slow reaction. Only<br>small amounts of<br>(VPC) |
| 14 | φCl, 22 g (0.2m)<br>$MeSi(OPr)_3$, 22 g (0.1m)<br>Mg, 4.8 g (0.2m) | Crystal $I_2$ | 109–113°/15 hr. | 8 hr. VPC:<br>MeφSi $(OPr)_2$/Meφ$_2SiOPr_2$/1,<br>little $MeSi(OPr)_3$ left |
| 15 | φCl, 100 g (0.9 m)<br>$MeSi(OPr)_3$, 88 g (0.4m)<br>Mg, 24 g (1 m) | THF, 56.8 g<br>$I_2$ Crystal | To 110°/18 hrs. | Distilled 128–130°C/<br>2mm, 27 g - Meφ$Si(OPr)_2$<br>130–1340°/ 2mm, 9 g. |

44 g (0.3 m) p-dichlorobenzene, 18 g (0.75 m) magnesium turnings, 132 g (0.75 m) dimethyldipropoxy silane, 21.6 g (0.3 m) tetrahydrofuran and a crystal of iodine. The mixture was heated to boiling and kept at reflux for about 12 hours. The temperature of the boiling mixture rose from 120° to 144° C much solids being formed and magnesium consumed during this period. The cooled reaction mixture was filtered easily and the solid filter cake washed with a little toluene. The filtrate was then distilled at atmospheric pressure to remove low boilers and then vacuum distilled. The cuts that were obtained

EXAMPLE II

A Barbier version of the Grignard coupling reaction was carried out in the presence of a coupling promoter, cuprous chloride (fresh). To a 3 l. flask equipped with a stirrer, condenser, thermometer, addition funnel, and a nitrogen inlet tube was added 105 g (4.3m) of magnesium turnings. The system was dried via flaming under a blanket of nitrogen. A stock solution of the reactants was prepared by dissolving 306 g (2.1m) of paradichlorobenzene in 734 g (4.1m) of di-n-propoxydimethylsilane (99.3% by GC) and 127 ml (0.75m) of tetrahydrofuran. Approximately 25% (300 mls.) of said stock solution was then added to the flask along with 1.5 g (0.015 m) of cuprous chloride (0.5 weight % on φ Cl₂) and a crystal of iodine. The contents of the vessel were heated to 132° C, the reaction initiated and the system quickly exothermed to 137° C. The balance of the stock solution was slowly added over a 3 hour period; no heat was applied during the first 1¼ hours of said period. Heating was resumed when the pot temperature subsided to 131° C, and the temperature was increased to 137°-138° C and the system refluxed for 10¼ hours. Aliquots were removed periodically and analyzed via GC, the results were:

| Reaction Time | Product %[C₃H₇OSi(Me)₂]₂φ |
|---|---|
| 3 hr. & 16 min. | 23.3% |
| 4 hr. & 16 min. | 52.3% |
| 5 hr. & 16 min. | 61.6% |
| 6 hr. & 1 min. | 71.1% |
| 12 hr. & 41 min. | 80.6% |

The total reaction time was 12 hours and 41 minutes, the system was cooled down to room temperature. The product was decanted away from the salt cake. The salt was washed with dry toluene and the washings were combined with the crude. The toluene was stripped off and the crude distilled under vacuum to provide 510 g (78% recovered yield) of 1,4-bis(n-propoxydimethylsilyl) benzene, b.p. 140°-142° C/5 mm.

EXAMPLE III

The synthesis procedure followed was the same as Example II, except for the scaleup to a larger batch size and the use of 0.71 weight % of cuprous chloride.

Magnesium turnings (478 g, 19.7 m) in a 12 l, flask were dried as described in Example II. The reactant stock solution was prepared by dissolving 1400 g (9.7m) of para-dichlorobenzene in 3700 g (21m) of di-n-propoxydimethylsilane and 515 g (7.2 m) of tetrahydrofuran. Fresh cuprous chloride (10.0 g, 0.10 m), a crystal of iodine, and 300 ml of the stock solution were added to the magnesium turnings. The vessel was heated to 132° C to initiate the reaction. The remaining stock solution was added over a 3 hour period and the system was refluxed at 137°-144° C for a total of 12¾ hours. The crude product was decanted away from the salt. The salt cake was washed with dry toluene and the washings and crude were combined and flash distilled. A crude product, 2563 g (83.9% yield) was obtained; subsequent fractionation gave 2412 g (79% recovered yield) of 1,4-bis(n-propoxydimethylsilyl)benzene, b.p. 140°-142° C/5 mm vacuum.

We claim:

1. An improved process for producing an aromatic containing silicone compound comprising (a) reacting a aromatic organic compound of the formula, $RX_a$ with a silicone compound of the formula, $R_b'$ Si $Z_{4-b}$ in the presence of molar quantities of Mg and from 0.5 up to 1 mole of a promoter per mole of the aromatic compound which is tetrahydrofuran wherein a portion of the reactants are added to the reaction chamber and then adding from 0.1 to 1% by weight of the total reactants of $Cu_2Cl_2$ as a coupler and then after a reaction period of time of 1 to 5 hours there is mixed into the reaction mixture the remaining portion of the reactants; and (b) distilling out the desired product where R is selected from the class consisting of monovalent and divalent mononuclear and binuclear aryl radicals, X is chlorine, a is a whole number that varies from 1 to 4, R' is a radical selected from the class consisting of monovalent hydrocarbon radicals. Z is selected from the class consisting of halogen and hydrocarbonoxy radicals and b varies 0 to 3.

2. The process of claim 1 wherein the reaction in step (a) is carried out at a temperature in the range of 100°-200° C for a period of time varying from 7 to 24 hours.

3. The process of claim 2 wherein the reaction is carried out at a temperature in the range of 100° to 160° C.

4. The process of claim 3 wherein there is present at least one mole of Mg for every mole of the aromatic compound.

5. The process of claim 4 comprising initiating the reaction in step (a) by adding a crystal of an iodine compound.

6. The process of claim 1 wherein further comprising adding to the initial reaction mixture a crystal of an iodine compound.

7. The process of claim 1 wherein the second portion of the reactants are added to reaction mixture after a period of reaction time varying from 1 to 5 hours.

8. The process of claim 1 wherein in the aromatic compound the R radical is phenylene.

9. The process of claim 8 wherein the aromatic compound is p-dichlorobenzene.

10. The process of claim 9 wherein in the silicon compound R' is methyl, Z is a radical selected from the class consisting of alkoxy radicals and phenoxy radicals of 1 to 8 carbon atoms.

11. The process of claim 10 wherein b is 2.

12. The process of claim 11 wherein the desired reaction product has the formulas,

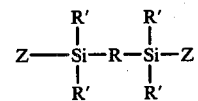

wherein R, R' and Z is as previously defined.

13. The process of claim 12 wherein the desired product is obtained in at least 50% by weight yield.

14. An improved process for producing a compound of the formula,

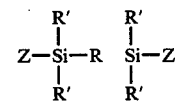

in at least 50% yield comprising (a) first adding and reacting a portion of the following ingredients which comprise an aromatic organic compound of the formula, $RX_a$ with a silicon compound of the formula, $R_b$ Si $Z_{4-b}$ in the presence of at least 2 moles of Mg per mole of the aromatic organic compound and from 0.5 to up to 1 mole of the catalytic promoter tetrahydrofuran per mole of the aromatic organic compound with from 0.1 to 1% by weight of the total reactants of $Cu_2Cl_2$ (b heating the reaction mixture in the range of 100° C to 160° C and (c) then after the reaction has been initiated adding the remaining portion of the ingredients after a period of time varying from 1 to 5 hours from the initia start of the reaction for a total reaction time varying from 7 to 24 hours and (d) distilling out the desired reaction product where R is a phenylene radical, $a$ is 2 such that the aromatic organic compound is p-dichlorobenzene and wherein R' is methyl, Z is selected from the class consisting of alkoxy and phenoxy radicals of 1 to 8 carbon atoms and $b$ is 2.

* * * * *